(12) United States Patent
Shubayev et al.

(10) Patent No.: US 7,223,257 B2
(45) Date of Patent: May 29, 2007

(54) PERCUTANEOUS VASCULAR ACCESS DEVICE

(76) Inventors: Igor Shubayev, 715 Gayley Ave., Suite 417, Los Angeles, CA (US) 90024; Elkana Elyav, 24 Kushnir Street, Ramot 3, Jerusalem (IL) 97280

( * ) Notice: Subject to any disclaimer, the term of this patent is extended or adjusted under 35 U.S.C. 154(b) by 104 days.

(21) Appl. No.: 10/931,942

(22) Filed: Aug. 31, 2004

(65) Prior Publication Data

US 2006/0047249 A1  Mar. 2, 2006

(51) Int. Cl.
*A61M 5/32* (2006.01)
(52) U.S. Cl. .................. 604/175; 604/93.01; 604/6.16
(58) Field of Classification Search ............... 604/6.1, 604/6.16, 7, 8, 19, 21, 27, 175, 246, 248; 623/1.1, 1.27; 251/343, 344
See application file for complete search history.

(56) References Cited

U.S. PATENT DOCUMENTS

| | | | |
|---|---|---|---|
| 3,626,938 A * | 12/1971 | Versaci ........................ 604/122 |
| 4,108,173 A * | 8/1978 | Slivenko et al. ............ 604/175 |
| 4,306,545 A * | 12/1981 | Ivan et al. ................... 128/887 |
| 4,417,888 A * | 11/1983 | Cosentino et al. .......... 604/175 |
| 4,496,350 A * | 1/1985 | Cosentino ................... 604/175 |
| 4,822,341 A * | 4/1989 | Colone ........................ 604/175 |
| 4,898,669 A * | 2/1990 | Tesio .......................... 210/232 |
| 4,904,245 A * | 2/1990 | Chen et al. .................. 604/248 |
| 4,983,162 A * | 1/1991 | Metais et al. ................. 604/43 |
| 5,147,321 A | 9/1992 | Slonina et al. |
| 5,180,365 A | 1/1993 | Ensminger et al. |
| 5,226,879 A | 7/1993 | Ensminger et al. |
| 5,263,930 A | 11/1993 | Ensminger et al. |
| 5,281,199 A | 1/1994 | Ensminger et al. |
| 5,350,360 A | 9/1994 | Ensminger et al. |
| 5,417,656 A | 5/1995 | Ensminger et al. |
| 5,421,814 A * | 6/1995 | Geary ........................ 604/6.1 |
| 5,474,526 A * | 12/1995 | Danielson et al. ........... 604/6.1 |
| 5,476,451 A | 12/1995 | Ensminger et al. |
| 5,503,630 A | 4/1996 | Ensminger et al. |
| 5,520,643 A | 5/1996 | Ensminger et al. |
| 5,527,277 A | 6/1996 | Ensminger et al. |
| 5,527,278 A | 6/1996 | Ensminger et al. |
| 5,531,684 A | 7/1996 | Ensminger et al. |
| 5,542,923 A | 8/1996 | Ensminger et al. |
| 5,554,117 A | 9/1996 | Ensminger et al. |
| 5,556,381 A | 9/1996 | Ensminger et al. |
| 5,713,859 A | 2/1998 | Finch, Jr. et al. |
| 5,755,780 A | 5/1998 | Finch, Jr. et al. |
| 5,792,123 A | 8/1998 | Ensminger et al. |
| 5,931,829 A | 8/1999 | Burbank et al. |
| 5,954,691 A | 9/1999 | Prosl |
| 6,007,516 A | 12/1999 | Burbank et al. |
| 6,042,569 A | 3/2000 | Finch, Jr. et al. |
| 6,056,717 A | 5/2000 | Finch et al. |

(Continued)

*Primary Examiner*—Cris Rodriguez
*Assistant Examiner*—Paul Smith
(74) *Attorney, Agent, or Firm*—Jones Day

(57) ABSTRACT

The present invention generally relates to the design and use of implantable medical devices, and in particular to the design and use of an implantable device for establishing long-term access to a patient's blood circulation for extra corporeal treatment of blood, such as hemodialysis, hemofiltration, oxygenation of blood and other. A vascular access device is provided having a rotatable inner core positioned within a device body between first and second positions for diverting blood flow to an extra corporeal blood circuit.

6 Claims, 9 Drawing Sheets

U.S. PATENT DOCUMENTS

Figure 1:
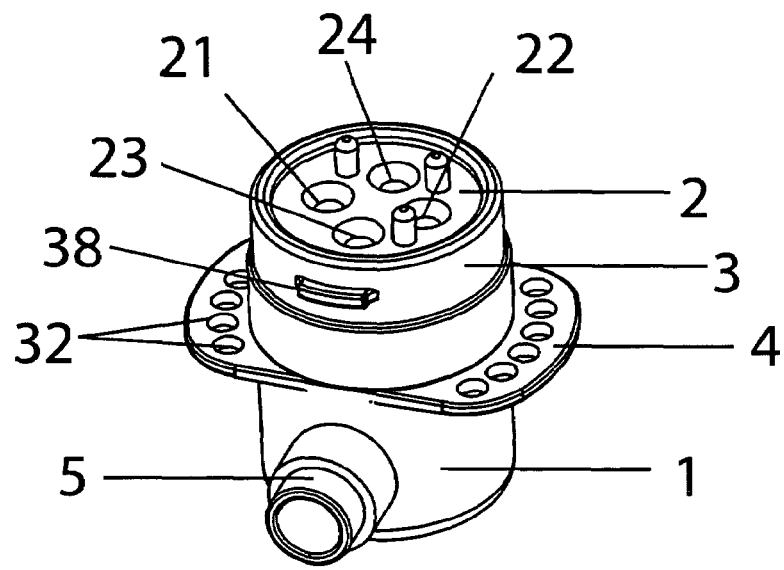

| | | |
|---|---|---|
| 6,206,851 B1 | 3/2001 | Prosl |
| 6,231,541 B1 * | 5/2001 | Kawamura ............... 604/93.01 |
| 6,238,369 B1 | 5/2001 | Burbank et al. |
| 6,258,079 B1 | 7/2001 | Burbank et al. |
| 6,436,089 B1 | 8/2002 | Danielson et al. |
| 6,506,182 B2 | 1/2003 | Estabrook et al. |
| 6,524,273 B2 * | 2/2003 | Kawamura ............... 604/93.01 |
| 6,569,117 B1 * | 5/2003 | Ziv et al. ............... 604/164.01 |
| 2004/0122346 A1 * | 6/2004 | Kawamura .................... 604/8 |

* cited by examiner

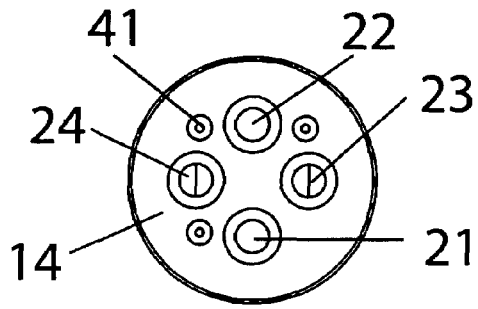
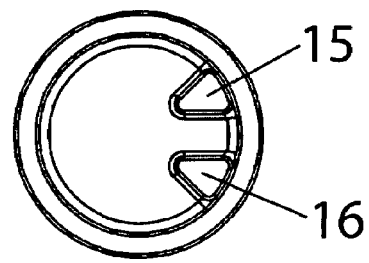
Fig. 8  Fig. 9
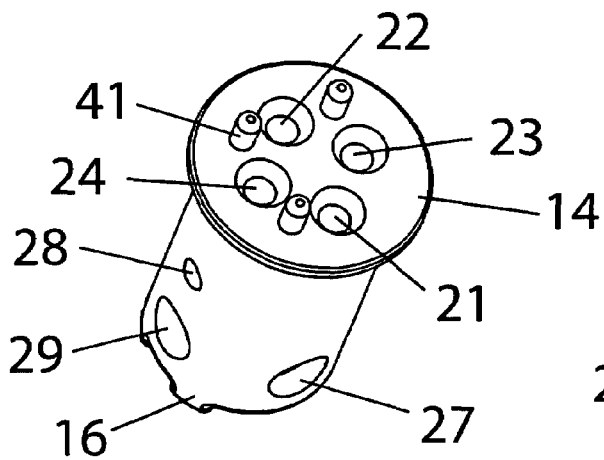
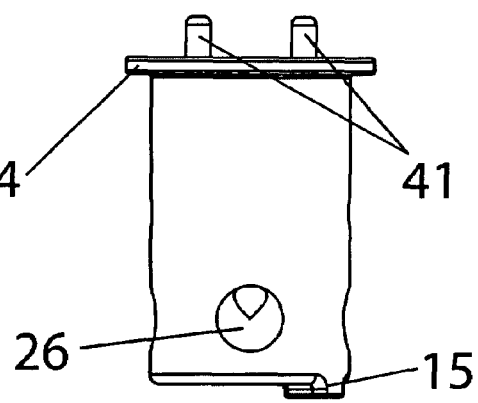
Fig. 10  Fig. 11
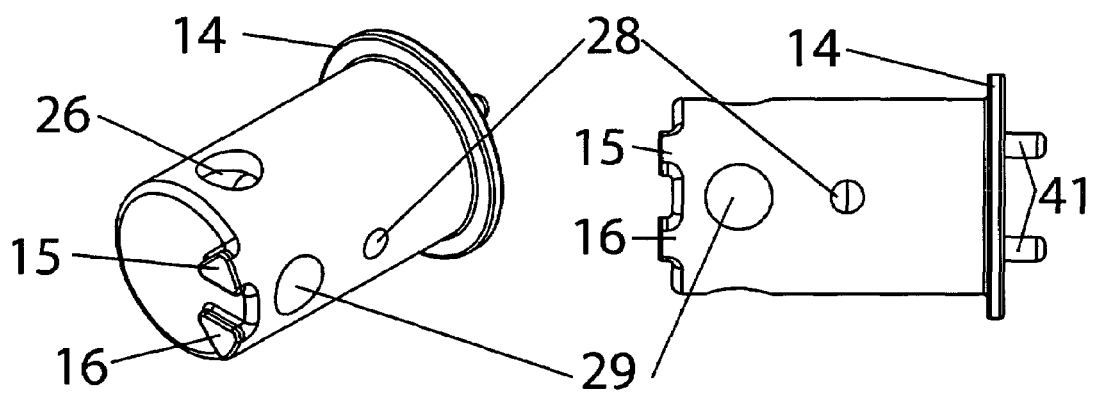
Fig. 12  Fig. 13

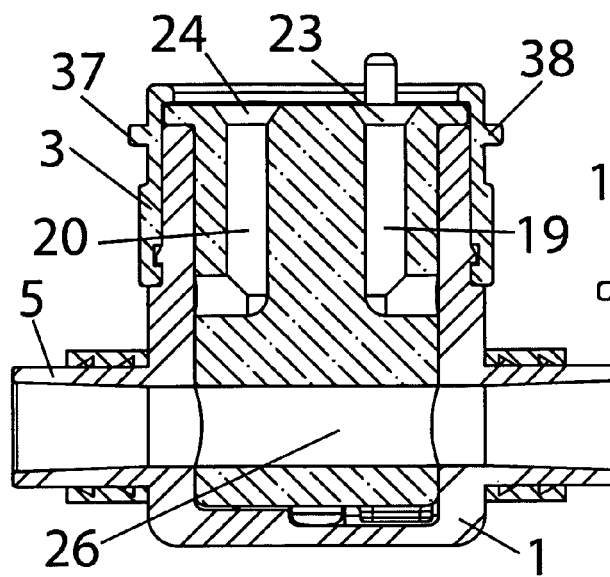
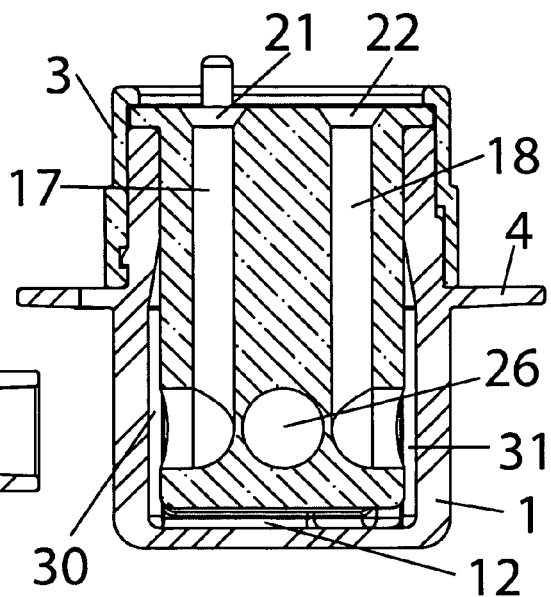
Fig. 24　　　Fig. 25
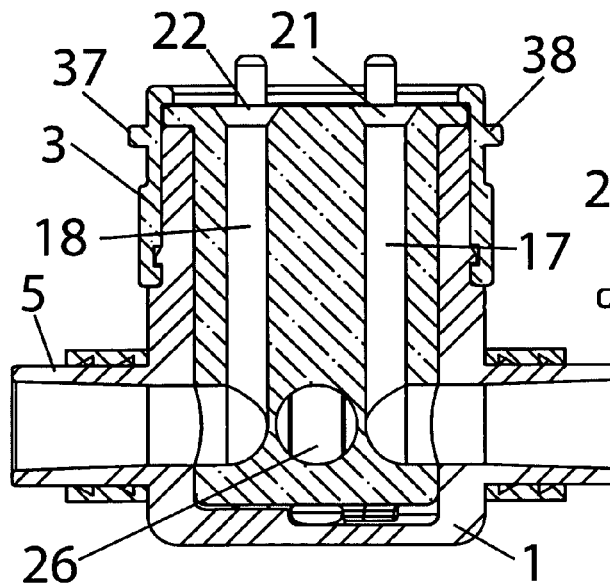
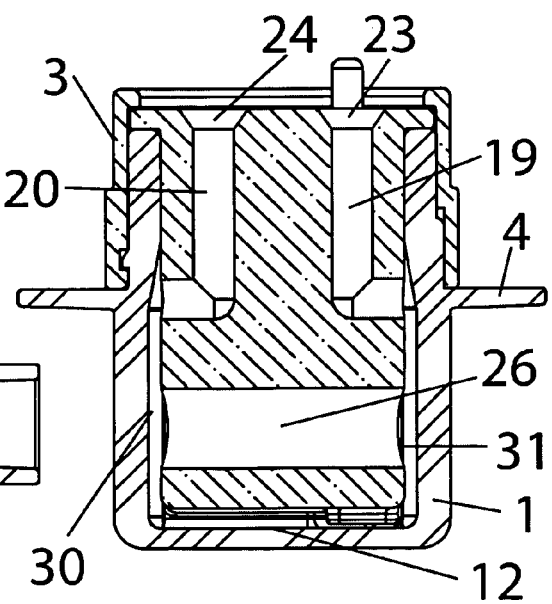
Fig. 26　　　Fig. 27

PERCUTANEOUS VASCULAR ACCESS DEVICE

BACKGROUND OF THE INVENTION

1. Field of the Invention

The present invention generally relates to the design and use of implantable medical devices, and in particular to the design and use of an implantable device for establishing long-term access to a patient's blood circulation for extra corporeal treatment of blood, such as hemodialysis, hemofiltration, oxygenation of blood and other.

2. Present State of Art

Despite several types of vascular access ports and devices proposed over recent years, vascular access remains one of the most problematic areas in treatment of patients requiring long-term access to their vascular system, such as hemodialysis. Almost all of those patients undergo a placement of one of the two, or both of widely accepted long-term vascular access options, during the life of their hemodialysis treatment. The first one is a surgical placement of an arteriovenous synthetic graft connecting patient's adjacent peripheral artery and vein to divert some of the arterial blood flow through the graft. The other is an arteriovenous fistula, a direct surgical connection between adjacent artery and vein with no synthetic conduit used. In both cases the blood circulation is accessed with two needles inserted though the skin either into the synthetic graph in the former case, or into the venous portion of an arteriovenous fistula in the latter scenario. This is done during each hemodialysis session in order to circulate blood through the dialysis machine and back into the patient. When artery is connected to a vein directly or through a synthetic graft, low-pressure low oxygen venous system is subjected to high pressure oxygenated arterial blood. Those conditions lead to a significant turbulence and damage of the vascular endothelium (cellular lining) on the venous side with subsequent narrowing of the vascular lumen, decrease of the flow in the access site and almost invariable occlusion of the established access. Needle stick injuries and infections also contribute to the loss of those types of accesses. As a result more than 60% of the synthetic grafts fail in the first year of use and nearly all of the remaining grafts fail in the second year. Arteriovenous fistulas have longer survival rates, but still very short of a desirable lifetime. Surgical intervention is warranted to reestablish the access each time it is occluded. Consequently, maintenance of vascular access for dialysis became a formidable and extremely costly obstacle in delivering lifesaving treatment for dialysis patients. More importantly, running out of vessels available for surgical access leaves no treatment options for some patients.

Several ports and access devices have been proposed over the recent years to address the significant shortcomings of the traditional vascular access types. However even though some of the solutions offer theoretical advantages over the traditional vascular accesses, none of the solutions found widespread application as treatment modalities either due to their inability to offer any practical advantages to existing solutions, or their prohibitively high rate of complications, mostly infections and clogging of the access. Thus creating an alternative vascular access for a long-term extra corporeal treatment of blood remains an extremely important task.

Long-term implantable vascular access solutions can be divided on subcutaneous, when an access port is implanted under the level of the skin, and percutaneous, when the access part is of the port is placed above the level of the skin to be accessed without the skin penetration. Presently available subcutaneous ports usually consist of a metal or synthetic housing which contains an access chamber and some type of a valve or a high-density, self-sealing septum, made of silicone rubber or similar material, which separates the access chamber from a conduit connecting the access port to a vein or other internal fluid conduit or cavity. The circulation is then accessed by the needle(s) inserted through the skin into the valve mechanism or through the septum to have a direct communication with the conduit(s) connecting the chamber with the blood vessel. After the blood treatment session the access is flushed with some type of the solution to prevent blood clotting and infection in the conduit.

Example of such a device is disclosed in a series of U.S. patents all titled "Implantable Access Devices" and issued to Ensminger et al. (U.S. Pat. Nos. 5,180,365 (Jan. 19, 1993), U.S. Pat. No. 5,226,879 (Jul. 13, 1993), U.S. Pat. No. 5,263,930 (Nov. 23, 1993), U.S. Pat. No. 5,281,199 (Jan. 25, 1994), U.S. Pat. No. 5,503,630 (Apr. 2, 1996), U.S. Pat. No. 5,350,360 (Sep. 27, 1994), U.S. Pat. No. 5,417,656 (May 23, 1995), U.S. Pat. No. 5,476,451 (Dec. 19, 1995), U.S. Pat. No. 5,520,643 May 28, 1996, 5,527,277 (Jun. 18, 1996), U.S. Pat. No. 5,527,278 (Jun. 18, 1996) U.S. Pat. No. 5,531,684 (Jul. 2, 1996), U.S. Pat. No. 5,542,923 (Aug. 6, 1996), U.S. Pat. No. 5,554,117 (Sep. 10, 1996), U.S. Pat. No. 5,556,381 (Sep. 17, 1996), U.S. Pat. No. 5,792,123 (Aug. 11, 1998). Another example of subcutaneous port is marketed by Vasca, Inc. (U.S. Pat. No. 5,713,859 (Feb. 3, 1998), U.S. Pat. No. 5,755,780 (May 26, 1998), U.S. Pat. No. 5,931,829 (Aug. 3, 1999), U.S. Pat. No. 6,007,516 (Dec. 28, 1999), U.S. Pat. No. 6,042,569 (Mar. 28, 2000), U.S. Pat. No. 6,238,369 (May 29, 2001) U.S. Pat. No. 6,056,717 (May 2, 2000), U.S. Pat. No. 6,258,079 (Jul. 10, 2001)) and Biolink's Dialock system (U.S. Pat. Nos. 5,954,691 (Sep. 21, 1999), U.S. Pat. No. 6,206,851 (Mar. 27, 2001), U.S. Pat. No. 6,506,182 (Jan. 14, 2003)).

All of the above and similar solutions share some significant limitations that prevent widespread use of those devices. Those devices represent an improved version of regular indwelling catheters and inherit many of the complications associated with the use of the latter. An implanted catheter usually has to be placed in a central vein to achieve acceptable flow rates. Such placement creates conditions such as low-flow state and disruption of a laminar flow which known to be the cause of infection and thrombosis. In addition implanted catheter inserted or attached to a central vein is difficult to vigorously disinfect, which increases the risk of infection in the catheter. Moreover, the central vs. peripheral placement of those devices not only provides a higher risk of serious infectious complications such as endocarditic, but also makes it much more difficult to diagnose early signs of those complications. Recent improvements in battling the infection in those devices might make some of them a useful treatment option in limited number of patients, but they are unlikely to provide adequate long-term vascular access in the majority of rapidly growing number of patients requiring regular access to their circulation for many years.

Percutaneous catheters have an external port coming out of the skin of the patient, which eliminates the necessity of using needle sticks to access the vascular system. Hemapure U.S. Pat. No. 6,436,089 proposed Hemaport, a percutaneous port that provides a mechanism for needle-less access to a synthetic graft, connecting patient's peripheral artery and vein, similar to the traditional arteriovenous graft. Although addressing one of the disadvantages of the traditional access, needle puncture of the skin and the vessel, the design inherits all the other shortcomings of arteriovenous graft responsible for it's failures. In addition a percutaneous portion of any device is always subject to a higher risk of infection that prevented use of various types of ports over years. Hemaport design is not offering anything to suggest that the device will have any different fate in that regard than previous solutions, which in addition to inherited problems of a conventional arteriovenous graft makes it's practical use highly improbable.

Another variant of percutaneous device is described in U.S. Pat. No. 5,147,321. The device is a percutaneous rotation switch mechanism, which consists of a hollow metal cylinder with one end of it perpendicularly attached to the middle portion of another tubular conduit with two round openings connecting the two cavities, with another end being a part of a percutaneous portion of the device to provide a direct access to the lumen of the second conduit through the cavity of the first one. A tightly fit solid cylinder with two parallel longitudinal channels is placed inside the first cylinder and can be rotated 90° to switch between two positions. The first "ON" position is when the two channels are aligned to the two openings to create two conduits going through the first cylinder into the cavity of the second one. The second "OFF" position is when the channels are not aligned to the openings closing the lumen of the second cylinder off. During implantation a vascular graft or any other blood vessel is transversally cut and the second cylinder is placed between the split ends to align the lumen of the cylinder with the vascular lumen in a continuous fashion. When the switch is in "ON" position two parallel channels are established between extra corporeal space and the vascular lumen, providing the route for withdrawal and returning blood back to the circulation. By rotating the internal cylinder 90° to the OFF position the channels are not aligned to the openings closing the vascular lumen off. Although this design eliminates the necessity of needle sticks it has major limitations. It designed to be inserted in arteriovenous graft thereby it would retain all of the limitations of the traditional graft. More importantly, the openings connecting the channels to the vascular lumen are positioned closely to each other allowing for a significant recirculation, especially in low-pressure systems (if placed into the venous system), thereby making the treatment of the blood very inefficient.

None of the prior art devices provides the solution for identified problems with existing vascular accesses. In summary it is desirable to provide a device that would address all of the following issues:

1. Eliminate or reduce factors that lead to narrowing and occlusion of the access.
2. Provide an effective mechanism to prevent or decrease infections associated with the use of the device.
3. Provide sufficient blow flow rates for extra corporeal treatments, such as dialysis
4. Eliminate the necessity of the needle puncture of the skin and the device to ensure no long-term damage to the vessel or device.
5. Provide a better patient comfort with resulting improved patient compliance.
6. Ensure safety, robustness and easiness of use of the device

OBJECTS AND BRIEF SUMMARY OF THE INVENTION

An object of this invention is to provide long-term/ permanent vascular access that would allow the access to the patient's blood circulation for extra corporeal treatments without puncturing skin or a vessel for every treatment, therefore eliminate pain and complications associated with the use of needles Another object of this invention is to provide a vascular access that better preserves the preexisting hemodynamic conditions, such as laminar blood flow with no or low turbulence, normal venous pressure and cardiac output, thereby preventing many complications associated with changing of those conditions with most existing types of vascular access.

Another object of this invention is to provide the mechanism that would allow diverting all of the blood flow in the target blood conduit into extra corporeal circulation, such as a dialysis machine, to allow higher blood flows for extra corporeal circulation, permitting more rapid, frequent and effective blood treatments.

Another object of this invention is to provide a mechanism for vigorous cleaning of the internal components of the device with large volume of fluid, such as antiseptic without entering the blood stream by providing a switch mechanism. This will prevent, or substantially decrease the incidence of infections, which every short of long-term implantable access inherently has.

Another object of this invention is to allow the placement of the permanent/long-term access into the blood vessels, such as large peripheral veins, like a femoral vein, which cannot be used for those purposes with existing types of accesses due a high complication rates. This will increase the scope of treatment options for many dialysis patients that have no other suitable vascular access sites.

Another object of this invention is to create a vascular access that is easy to use and safe enough to eventually be implemented as a home treatment modality for procedures like dialysis.

DRAWINGS

Figure 2:
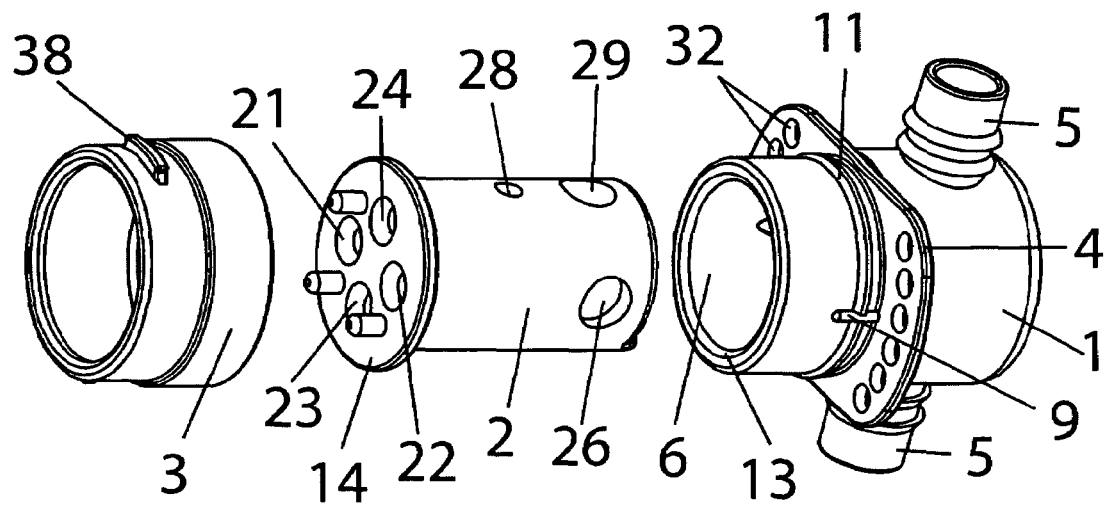
Figure 3:
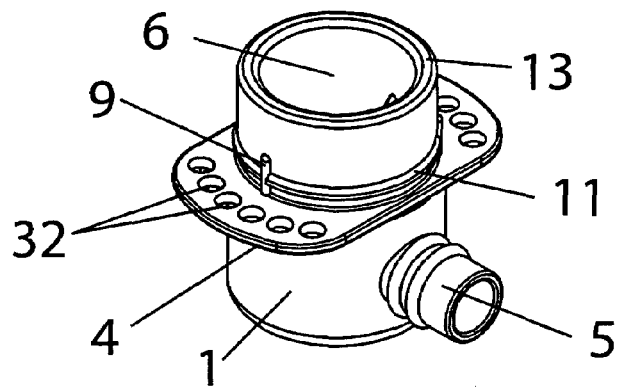
Figure 4:
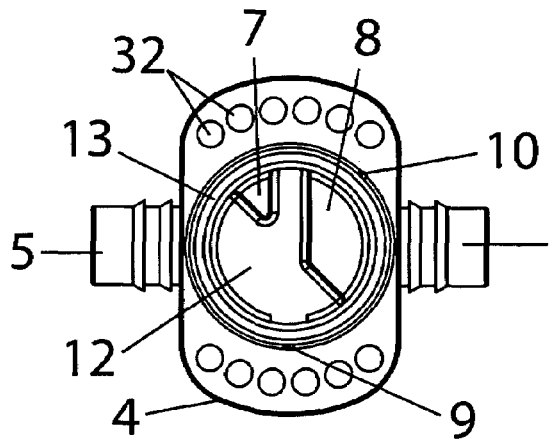
Figure 5:
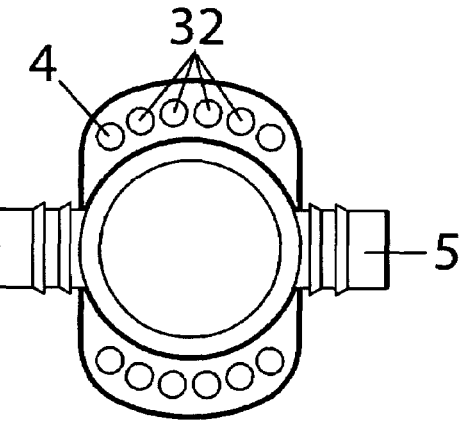
Figure 6:
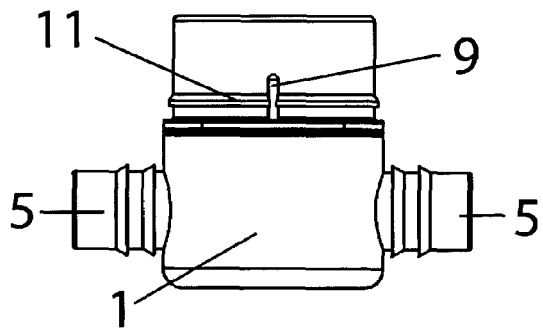
Figure 7:
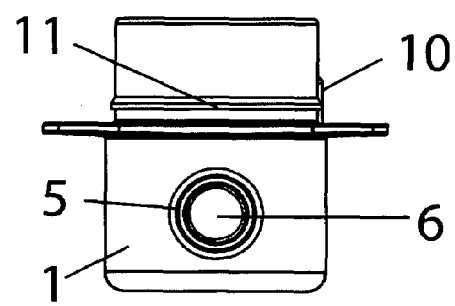
Figure 14:
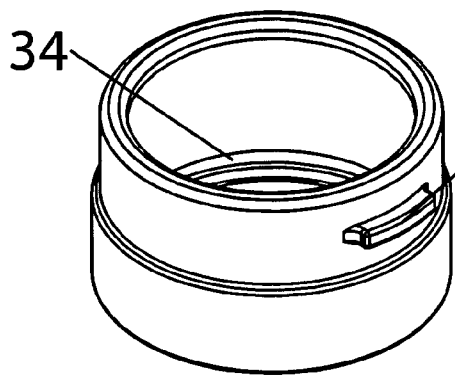
Figure 15:
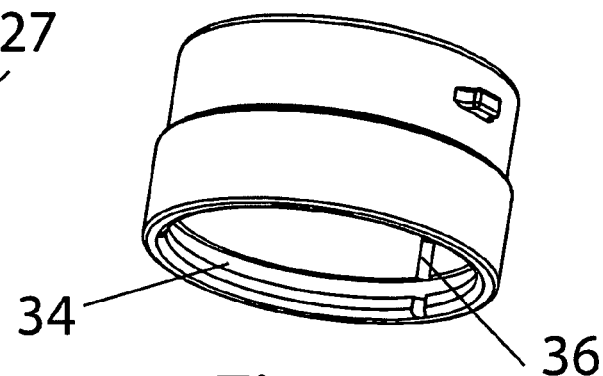
Figure 16:
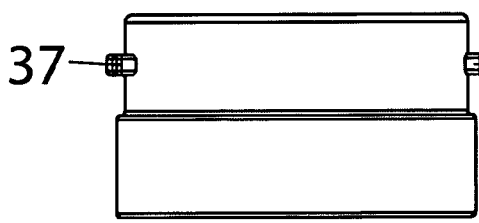
Figure 17:
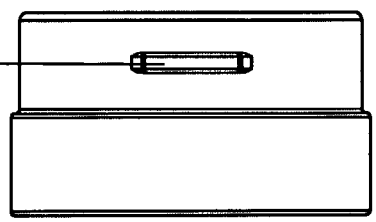
Figure 18:
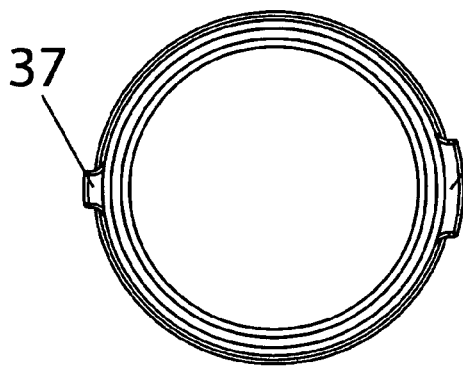
Figure 19:
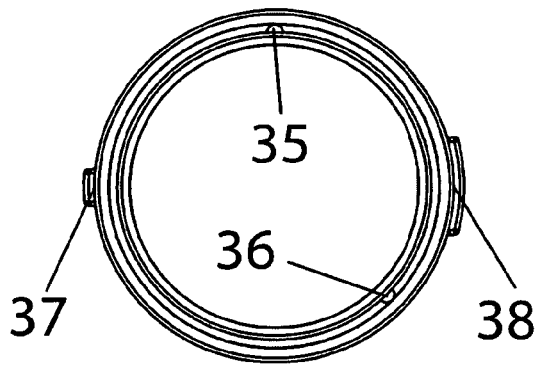
Figures 20, 21:
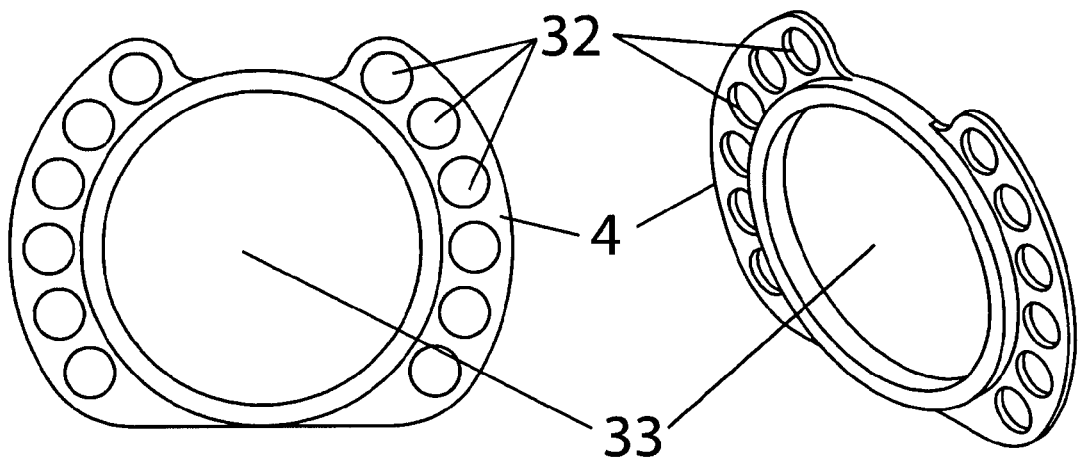
Figures 22, 23:
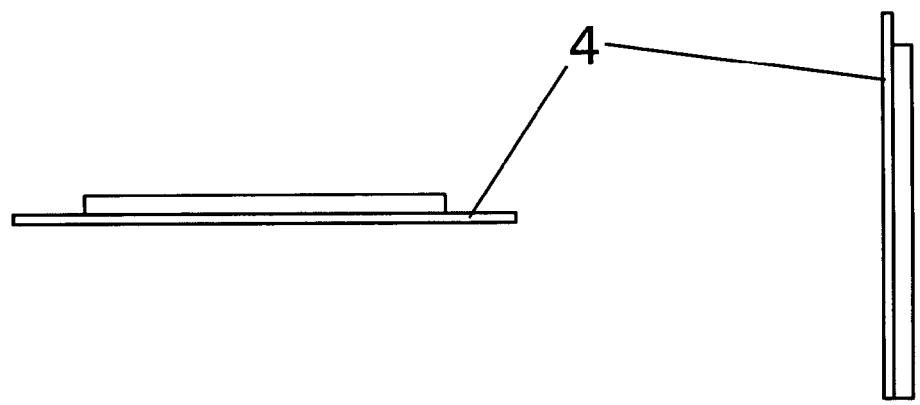
Figure 28:
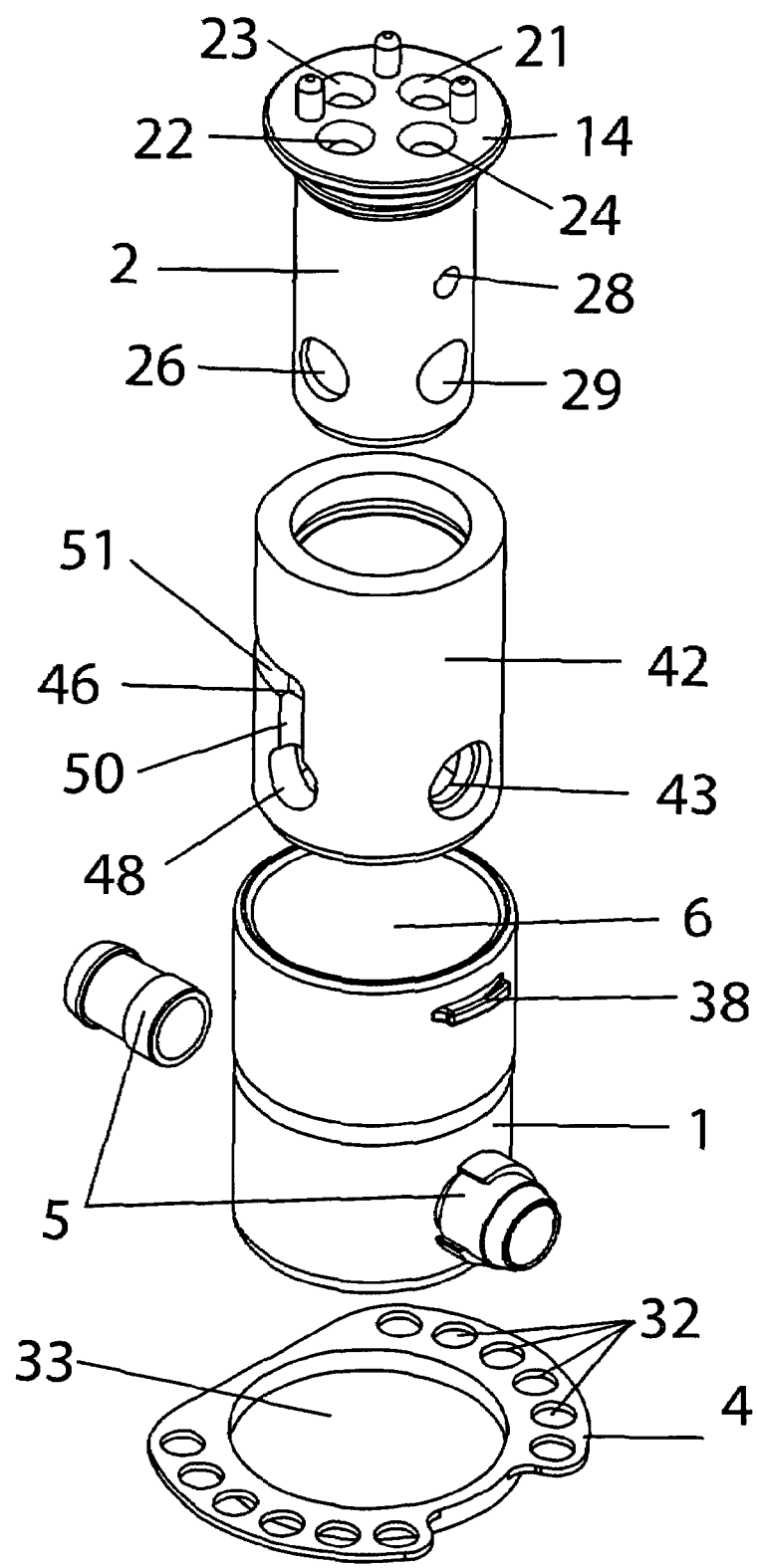

FIG. 1 General view of the device
FIG. 2 Assembly of the device
FIG. 3 Angle view of the Device Body
FIG. 4 Top view of the Device Body
FIG. 5 Bottom view of the Device Body
FIG. 6 Front view of the Device body
FIG. 7 Side view of the Device Body
FIG. 8 Top view of the Inner Core
FIG. 9 Bottom view of the Inner Core
FIG. 10 Top angle view of the Inner Core
FIG. 11 Front view of the Inner Core
FIG. 12 Bottom/side angle view of the Inner Core
FIG. 13 Side view of the Inner Core
FIG. 14 Top angle view of the Outer Body
FIG. 15 Bottom angle view of the Outer Body
FIG. 16 Front view of the Outer Body
FIG. 17 Side view of the Outer Body
FIG. 18 Top view of the Outer Body
FIG. 19 Bottom view of the Outer Body
FIG. 20 Top view of the Anchor
FIG. 21 Top angle view of the Anchor
FIG. 22 Front angle view of the Anchor
FIG. 23 Side view of the Anchor
FIG. 24 Front cross-sectional view of the device in "OFF" position
FIG. 25 Side cross-sectional view of the device in "OFF" position
FIG. 26 Front cross-sectional view of the device in "ON" position FIG. 27 Side cross-sectional view of the device in "ON" position FIG. 28 Assembly of the device (alternative description)

Figures 29, 30:
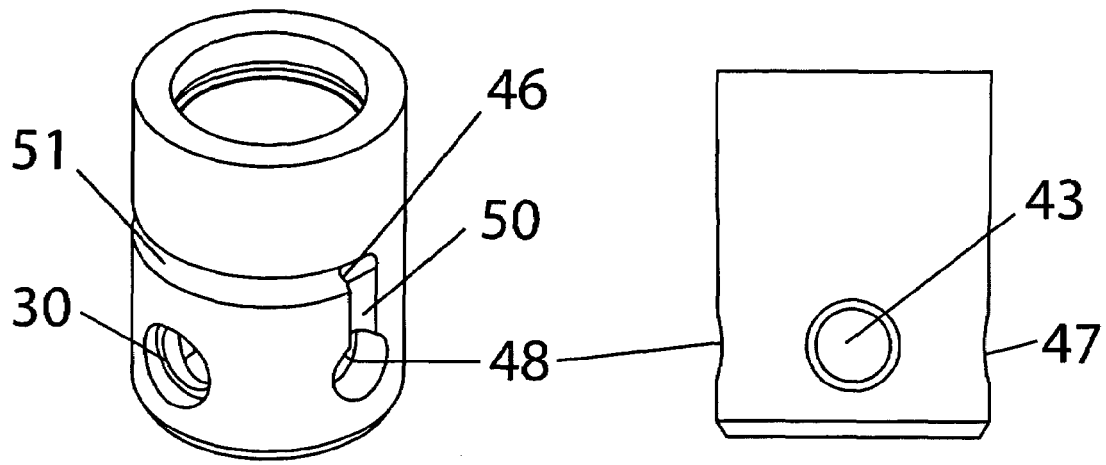

FIG. 29 Front angle view of the Sleeve

FIG. 30 Left view of the Sleeve

Figures 31, 32:
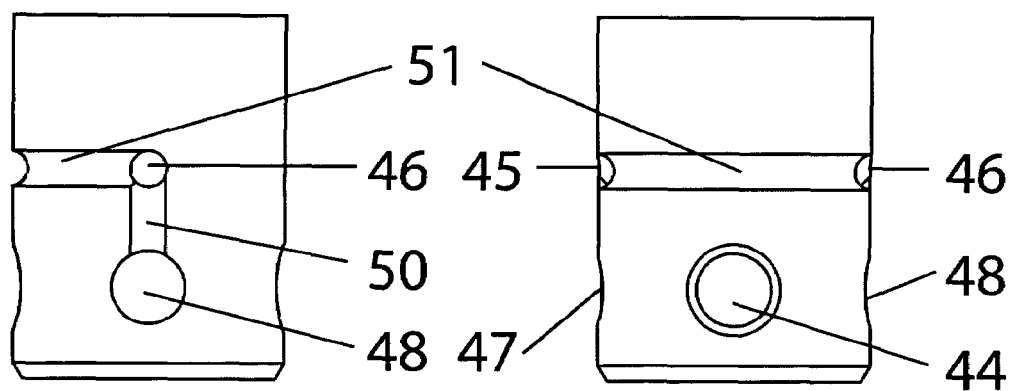

FIG. 31 Front view of the Sleeve

FIG. 32 Right view of the Sleeve

Figure 33:
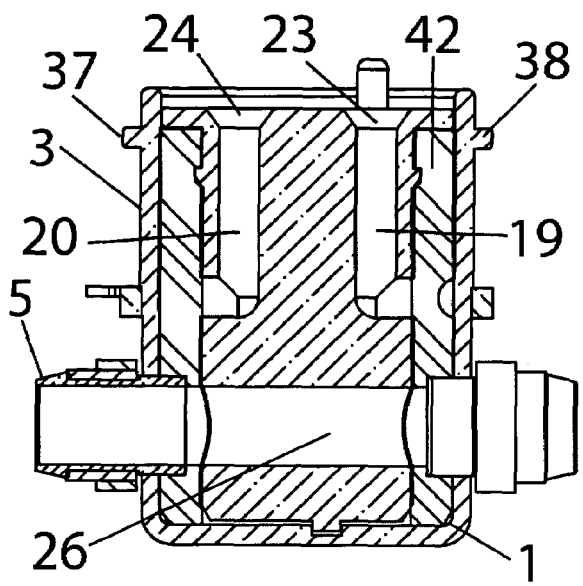

FIG. 33 Front cross-sectional view of the device in "OFF" position

Figure 34:
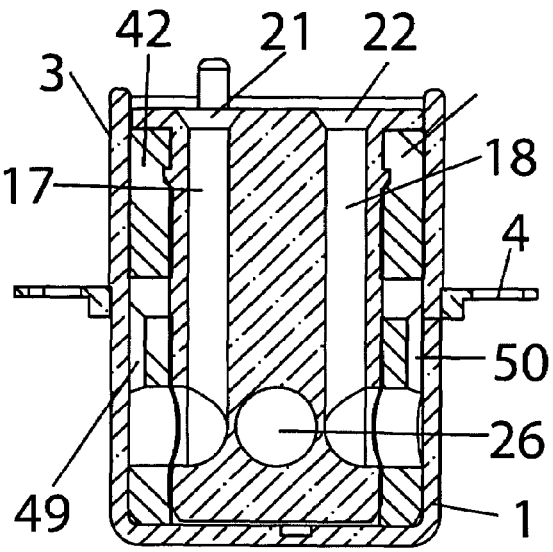

FIG. 34 Side cross-sectional view of the device in "OFF" position

Figure 35:
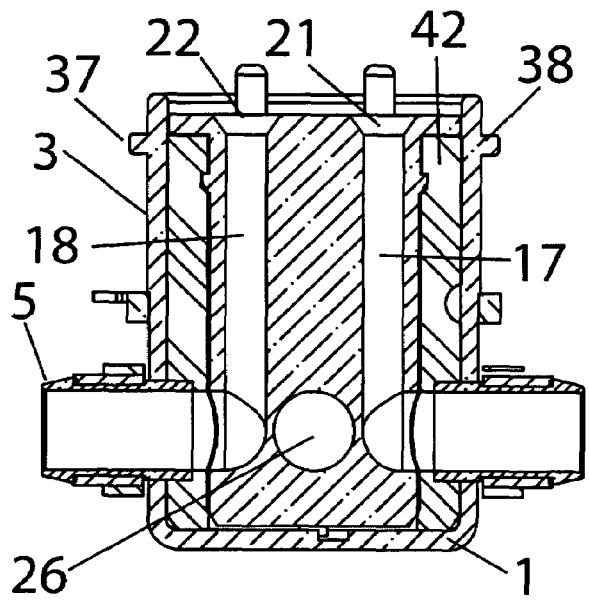

FIG. 35 Front cross-sectional view of the device in "ON" position

Figure 36:
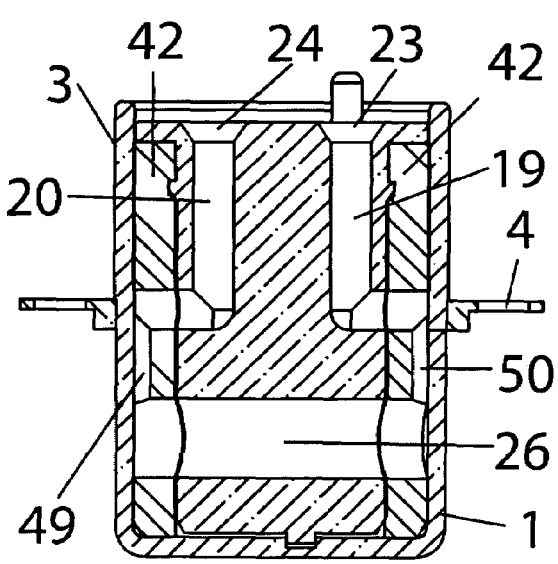

FIG. 36 Side cross-sectional view of the device in "ON" position

DETAILED DESCRIPTION

Preferred Embodiment (FIGS. 1-27)

As illustrated on FIGS. 1 and 2 the device consists of the following components: Device Body 1, Inner Core 2, Outer Body 3, Anchor 4 and Nipples 5. The Device Body 1 as illustrated in FIGS. 2-7 represents a hollow cylinder, which could be made of metal, like titanium, stainless steel, synthetic material, like polyurethane or any other biocompatible material. The bottom portion the Device Body is closed whereas the top portion open. Two smaller hollow tubular structures, the nipples 5 extend perpendicularly from the exterior of the lower portion of the Device Body (FIGS. 4-6). The lumen of each nipple opens in the cavity 6 of the Device Body directly opposite of each other (FIGS. 3,7). The Inner Core 2 (FIGS. 8-13) is a solid cylinder with a thin disk-like top 14 that has a larger diameter than the main cylinder (FIGS. 2,10-13). Inner core is tightly fit into the Device Body with the disk-like top 14 fitting in the Device Body Top Groove 13 (FIGS. 2-4) of the Device Body. The bottom of the Inner Core has two protrusions 15 and 16 (FIGS. 9, 11-13), which fit in the Device Body Bottom Groove 12. The Inner Core can be rotated inside the Device Body at 90° maintaining the hermetical junction with the Inner Body, with Inner Core protrusions 15 & 16 moving inside the Device Body Bottom Groove 12 between Device Body Bottom Protrusions 7 and 8 (FIG. 4). The Inner Core contains two pairs of conduits 17, 18, and 19, 20 (FIGS. 24-27) going longitudinally and parallel to each other in the top portion of the Inner Core each having a respective opening 21, 22, 23, 24 on the top surface of the Inner Core ((FIGS. 1,2,8,10, 24-27). In the bottom portion of the Inner Core the conduits angle towards the exterior of the Inner Core forming respective openings on the outer surface of the Inner Core 16 and 17 (FIGS. 10-13). Each conduit has an opening on the same level as its pair and directly opposite to it. As illustrated in FIGS. 10-13 and 24-27, axis of the openings 21, 22 of conduits 17, 18 is perpendicular to the axis of the openings 23, 24 of the conduits 19, 20 in (FIGS. 10,12). In addition the axis going through the openings 21, 22 is closer to the bottom than axis going through the openings 23, 24 (FIGS. 10,12) and can be aligned to the axis of the Nipples 5 of the Device Body 1 in the way that both of those conduits 17 and 18 can be aligned to form a continues conduit with the respective Nipple when the access is in ON position (FIG. 26). The bottom portion of the Inner Core contains the Single Inner Core Conduit 29 (FIGS. 2,10,12,13,24-27) that goes diametrically through the bottom of the Inner Core 2 at the same level as openings 21, 22 and perpendicular to it. Thus, when the Inner Core rotates to OFF position, conduit 18 forms a continuous passageway with both Nipples (FIG. 24).

The inner surface of the Device Body contains Longitudinal Side Grooves 30, 31 (FIGS. 25, 27) directly opposite of each other in the plane that is perpendicular to the plane of the Nipples 5. Those grooves 30, 31 and Device Body Bottom Groove 18 form a continuous conduit with the Inner Core Conduits 17 and 18 when the Inner Core is in OFF position (FIG. 25), and with Inner Core Conduits 19 and 20, when the Inner Core is in ON position (FIG. 27). The conduits formed by the grooves 30, 31 and 18 are used to flush large volumes of fluid to clean all the internal conduits in the switch mechanism. Because this washing loop is completely isolated from the circulation through the target vessel, it is possible to use cleaning solutions and volumes that could not be used in other ports and catheters, thereby providing an important mechanism in preventing infectious complications. Rod-like Inner Core External Protrusions 41 on the top surface of the Inner Core (FIGS. 8, 10, 11, 13) are used to guide the connector necessary for the attachment of the vascular access device to the extra corporeal circulation. The Anchor 4 could be in a shape of regular or irregular solid disk made of metal or any other material with different degrees of flexibility depending on the implantation site and other parameters. The Control Anchor Opening 33 (FIGS. 20,21) is used to fit the Anchor over the upper part of the Device Body 1. The place of fixation of the Anchor to the Device Body could be made adjustable to regulate the length of the Device Body external to the Anchor to allow variable depths of device implantation. The Fenestrations 32 (FIGS. 1-5,20,21) cover most of the surfaces of the Anchor to allow tissue overgrowth through the Anchor 4 for a firm integration of the device with the surrounding tissues. The Anchor 4 can also be made of a mesh-type material for those purposes. The Outer Body 3 is a short hollow cylindrical structure with the Outer Body Centrifugal Groove 34 (FIGS. 14, 15) going along the circumference of the internal surface of the bottom part of the Outer Body 3. Two Outer Body Internal Grooves 35, 36 (FIGS. 15,19) go through the bottom part of the internal surface of the Outer Body. Outer Body in tightly fit on top of the Device Body (FIG. 2) with Outer Body Internal Grooves 35, 36 fitting the protrusions 9, 10 and the Outer Body Centrifugal Groove 34 fitting the Device Body Centrifugal Protrusion 11 (FIGS. 3, 4, 6) to guide and firmly fix the Outer Body to the Device Body. Protrusions 37, 38 (FIGS. 14-19) are used for the attachment of the connector during the use of the device and the device cover, when the device is not in use. The device could be made without the Outer Body, with the Device Body assuming the functions of the latter. However a detachable Outer Body allows to use a material with different mechanical and biocompatibility qualities than the rest of the access in a place where skin integration is an important consideration. In addition being the most exposed part of the access the Outer Body could be changed if necessary without going through a major procedure of replacing the complete access. The vascular access can be implanted in any target fluid conduit, including any vessel or graft. The target vessel is attached to the Nipples 5 to form a continuous conduit. The access is implanted in a way that the Outer Body 3 with the top surface of the Inner Core 2 is placed above the skin level. The rotational valve has two positions: The unaltered flow position OFF (FIGS. 24, 25) when blood flows unaltered through the target vessel, and the controlled flow position ON (FIGS. 26, 27) when blood is passed through extra corporeal circuit before returning back to the targeted vessel.

When connecting to the dialysis machine the access connector attaches to the access by means of the Outer Body Protrusions 37, 38 (FIGS. 14-19) preventing accidental removal of the connector. In the unaltered flow OFF position blood flows through the target vessel and the access conduit formed by the Nipples 5 and Single Inner Core Conduit 29 (FIG. 24) preserving laminar flow. Cleaning solution flows through another access conduit formed by Inner Core Conduits 17, 18 and the Device Body Grooves 12, 30, 31, cleaning them out and readying the access for dialysis. A 90-degree turn puts the access into the controlled flow, ON position. In this position the target vessel forms the conduit with Inner Core Conduits 19, 20 and all the blood going trough the target vessel is circulated from the vessel through the dialysis machine and back into the vessel (FIG. 26). At the same time cleaning solution circulates through the access conduit formed by Single Inner Core Conduit 29 and the Device Body Grooves 30, 31. Upon completion of the blood treatment the switch is returned to the initial position. Cleaning solution is once again passed through the conduits of the access not carrying blood allowing for vigorous cleaning of all the internal components if the device that come in contact with blood at any point.

Description of Alternative Embodiments (FIGS. 28-36)

The alternative embodiment has an additional component, the Sleeve 42 (FIG. 28). The purpose of the Sleeve is to improve friction and sealing qualities of the Inner Core 2 and Device Body 1 integration if necessary. The Sleeve 42 (FIGS. 29-36) is a cylindrical hollow structure, which is tightly fit between the Inner Core 2 and the Device Body 1, and is firmly attached to the latter (FIG. 28). It has six round Sleeve Perforations 43, 44, 45, 46, 47, 48 (FIGS. 28-32) on the sides of the Sleeve to match in size and position the Internal Core Openings 25, 26, 27, 28, as well as the openings of the Single Inner Core Conduit 29 in the same order, when the Internal Core is in OFF position (FIGS. 33, 35). The First Longitudinal Sleeve Groove 49 connects Sleeve Perforations 45 and 47, and the Second Longitudinal Sleeve Groove 50 connects Sleeve Perforations 46 and 48 in the same way (FIGS. 29, 31, 34, 36). In addition Sleeve Perforations 45 and 46 are connected to each other by Transverse Sleeve Groove 51, which is going over the half of the Sleeve circumference (FIGS. 29, 31, 32). Those Longitudinal Sleeve Grooves 49 and 50 substitute the Device Body Side Grooves 30 and 31 in the preferred embodiment and the Transverse Sleeve Groove 51 substitutes the Device Body Bottom Groove 12, which are absent in this embodiment. When the access is in OFF position, the Inner Core Conduits 17 and 18 form the closed conduit through the Sleeve Grooves 49, 50, and 51 (FIG. 34) to allow the cleaning fluid to be circulated through them, while Single Inner Core Conduit 29 forms a continuous conduit with the target vessel through the Nipples 5 and Sleeve Perforations 47, 48 (FIG. 33). When the access is in ON position, the Inner Core Conduits 17 and 18 are aligned to the target vessel through the Nipples 5 and Sleeve Perforations 47, 48 (FIG. 35), while Inner Core Conduits 19 and 20 form a continuous conduit with Sleeve Grooves 49, 50, and 51 and Single Inner Core Conduit 29 to be washed with cleaning solution (FIG. 36).

What is claimed is:

1. An implantable vascular device comprising:
    a hollow cylindrical device body having a pair of hollow nipples, extending from the exterior of the valve body and in fluid communication with the interior space of the device body, the device body further having a passageway between the exterior of the inner core and the interior of the device body;
    rotatable cylindrical inner core positioned within the device body between a first positon and a second position, said inner core further including:
    a single channel passing through the inner core that positions the opposed nipples in fluid communication with each other, when the inner core is in the first position;
    a pair of openings;
    a first pair of conduits within the inner core each in fluid communication with the pair first openings in the inner core, when the inner core is in the first position, the first pair of conduits being further defined as being in fluid communication between said pair of first openings and hollow nipples when the inner core is in the second position; and
    a second pair of conduits within the inner core, each in communication with a second pair of openings within the inner core, the second pair of conduits also being joined in fluid communication by the passageway of the device body when the inner core is in the second position.

2. The implantable vascular device of claim 1, further comprising:
    a hollow outer body surrounding the inner body, the outer body having grooves for engagement of the inner body and outer body in a hermetical seal.

3. The implantable vascular device of claim 1, wherein the opposed pair of nipples have a common centerline, and the inner body has internal protrusions to limit the rotation of the inner body between the first and second positions.

4. The implantable vascular device of claim 3, wherein the inner body is rotated 90° between the first position and the second position.

5. The implantable vascular device of claim 2, further comprising:
    an anchor located between the inner core and the outer body, the anchor having a central opening to allow fitting the anchor about the exterior of the inner body.

6. The implantable vascular device of claim 2, wherein the anchor is further defined as having a plurality of fenestrations adapted for tissue ingrowth.

* * * * *